(12) United States Patent
Bornzin et al.

(10) Patent No.: US 6,721,601 B1
(45) Date of Patent: Apr. 13, 2004

(54) SYSTEM AND METHOD FOR AUTOMATIC ATRIAL CAPTURE DETECTION AND ATRIAL PACING THRESHOLD DETERMINATION

(75) Inventors: Gene A. Bornzin, Simi Valley, CA (US); Paul A. Levine, Santa Clarita, CA (US); Kenneth Valikai, Palos Verdes Pen., CA (US); Jason A. Sholder, Hartford, CT (US)

(73) Assignee: Pacesetter, Inc., Sylmar, CA (US)

(*) Notice: Subject to any disclaimer, the term of this patent is extended or adjusted under 35 U.S.C. 154(b) by 98 days.

(21) Appl. No.: 10/102,271

(22) Filed: Mar. 19, 2002

Related U.S. Application Data (63) Continuation of application No. 09/481,085, filed on Jan. 11, 2000, now Pat. No. 6,389,316.

(51) Int. Cl.[7] .................................................. A61N 1/37
(52) U.S. Cl. ........................................................ 607/28
(58) Field of Search .............................. 607/28, 27, 14, 607/11, 9

(56) References Cited

U.S. PATENT DOCUMENTS

| | | | |
|---|---|---|---|
| 4,686,988 A | 8/1987 | Sholder | 128/419 |
| 4,817,605 A | 4/1989 | Sholder | 128/419 |
| 4,940,052 A | 7/1990 | Mann et al. | 128/419 |
| 4,944,298 A | 7/1990 | Sholder | 128/419 |
| 5,350,410 A * | 9/1994 | Kleks et al. | 607/28 |
| 5,476,487 A * | 12/1995 | Sholder | 607/28 |
| 5,571,144 A * | 11/1996 | Schroeppel | 607/28 |
| 5,601,615 A * | 2/1997 | Markowitz et al. | 607/28 |
| 5,861,012 A * | 1/1999 | Stroebel | 607/28 |
| 6,101,416 A * | 8/2000 | Sloman | 607/28 |

\* cited by examiner

Primary Examiner—Kennedy Schaetzle (57) ABSTRACT

An implantable dual chamber stimulation device provides a novel detection scheme that automatically detecting atrial capture and performing an atrial pacing threshold assessment. The stimulation device preferably waits until the patient is at or near rest and monitors the patient's P-wave activity to determine a detection window where a next P-wave is expected to occur. The stimulation device then delivers an atrial pulse prior to the next detection window, and monitors the window to determine whether a P-wave occurs therein. If a P-wave does not occur, then atrial capture is present, while occurrence of a P-wave indicates absence of atrial capture. If atrial capture is absent, the stimulation device automatically determines an appropriate atrial pacing threshold by monitoring the detection window while adjusting the stimulation pulse energy level. Advantageously, the present invention further employs a "bottom-up" adjusting scheme which starts at a low energy level, below the expected atrial pacing threshold, and increases the energy level until atrial capture is detected, thus saving energy and further avoiding corruption by large polarization signals. The latter feature is compatible with the present detection scheme and conventional evoked response detection schemes. The new atrial pacing threshold is then set at the atrial pulse level at which atrial capture was effectuated plus a predetermined safety margin.

15 Claims, 4 Drawing Sheets

SYSTEM AND METHOD FOR AUTOMATIC ATRIAL CAPTURE DETECTION AND ATRIAL PACING THRESHOLD DETERMINATION

CROSS-REFERENCE TO RELATED APPLICATIONS

This application is a continuation of U.S. Pat. application Ser. No. 09/481,085, filed Jan. 11, 2000. Now U.S. Pat. No. 6,389,316

FIELD OF THE INVENTION

The present invention relates in general to implantable cardiac stimulation devices, including bradycardia and antitachycardia stimulation devices, defibrillators, cardioverters and combinations thereof that are capable of measuring physiological data and parametric data pertaining to implantable medical devices. More particularly, this invention relates to a system and method for automating detection of atrial capture and determination of an atrial pacing threshold in an implantable cardiac stimulation device.

BACKGROUND OF THE INVENTION

Implantable cardiac stimulation devices (such as pacemakers, defibrillators, and cardioverters-) are designed to monitor and stimulate the heart of a patient that suffers from a cardiac arrhythmia. Using leads connected to a patient's heart, these devices typically stimulate the cardiac muscles by delivering electrical pulses in response to detected cardiac events which are indicative of a cardiac arrhythmia. Properly administered therapeutic electrical pulses often successfully reestablish or maintain the heart's regular rhythm.

Implantable cardiac stimulating devices can treat a wide range of cardiac arrhythmias by using a series of adjustable parameters to alter the energy, the shape, the location, and the frequency of the therapeutic pulses. The adjustable parameters are usually defined in a computer program stored in a memory of the implantable device. The program (which is responsible for the operation of the implantable device) can be defined or altered telemetrically by a medical practitioner using an external implantable device programmer.

Modern implantable devices have a great number of adjustable parameters that must be tailored to a particular patient's therapeutic needs. One adjustable parameter of particular importance in stimulation devices is the stimulus energy (i.e., the pulse amplitude and pulse width) which can be programmed to new values in response to changes in capture threshold. "Capture" is defined as a cardiac depolarization and contraction of the heart in response to a stimulation pulse. When a stimulation pulse stimulates either a patient's atrium or ventricle during an appropriate portion of a cardiac cycle, it is desirable to have the heart properly respond to the stimulus provided. Every patient has a "capture threshold" which is generally defined as the minimum amount of stimulation energy necessary to effect capture. Capture should be achieved at the lowest possible energy setting yet provide enough of a safety margin so that should a patient's threshold increase, the output of an implantable stimulation device (i.e. the pacing stimulus energy) will still be sufficient to maintain capture. Dual chamber stimulation devices may have different atrial and ventricular pacing stimulus energies that correspond to different atrial and ventricular capture thresholds, respectively.

The earliest stimulation devices had a predetermined and unchangeable pacing stimulus energy, which proved to be problematic because the capture threshold is not a static value. The capture threshold also may be affected by a variety of physiological and other factors. For example, certain cardiac medications may temporarily raise or lower the threshold from its normal value. In another example, fibrous tissue that forms around stimulation device lead tips within several months after implantation may cause an increase in the capture threshold. To avoid loss of capture, the earliest stimulation devices were preset to deliver pacing pulses at the maximum energy available. As a result some patients experienced discomfort because of the high level of stimulation. Furthermore, such stimulation pulses consumed extra battery resources, thus shortening the useful life of a stimulation device.

When programmable stimulation devices were developed, the pacing stimulus energy was implemented as an adjustable parameter that could be set or changed by a medical practitioner. Typically, such adjustments were effected by the medical practitioner using an external programmer capable of communication with an implanted stimulation device via telemetry or via a magnet applied to a patient's chest. The particular setting for the stimulation device's pacing threshold was usually derived from the results of extensive physiological tests performed by the medical practitioner to determine the patient's capture threshold, from the patient's medical history, and from a listing of the patient's medications. This improvement in adjustable pacing stimulus energy permitted programming to lower values that tended to conserve battery energy and extend the useful service life of the stimulation device.

Also, patients who experienced discomfort due to excessively high stimulus energy pulses could have the stimulus energy safely decreased thus, lessening the incidence of surgical revision of the pacing system. While the adjustable pacing stimulus energy feature proved to be superior to the previously known static stimulus energy, some significant problems remained unsolved. In particular, when a patient's capture threshold changed, the patient was forced to visit the medical practitioner to adjust the pacing stimulus energy accordingly.

To address this pressing problem, manufacturers have developed advanced stimulation devices that are capable of determining a patient's capture threshold and automatically adjusting the stimulation pulses to a level just above that which is needed to maintain capture. This approach, referred to herein as "autocapture", improves the patient's comfort, reduces the necessity of unscheduled visits to the medical practitioner, and greatly increases the stimulation device's battery life by conserving the energy used for stimulation pulses.

A common technique used to determine whether capture has been effectuated is to monitor the patient's cardiac activity and to search for presence of an "evoked response" following a stimulation pulse. The evoked response is an electrical event that is the response of the heart to the application of a stimulation pulse thereto. The patient's heart activity is typically monitored by the stimulation device by keeping track of the stimulation pulses delivered to the heart and by examining, through the leads connected to the heart, electrical signals that are manifest concurrent with depolarization or contraction of muscle tissue(myocardial tissue) of the heart. The contraction of atrial muscle tissue is evidenced by the generation of a P-wave, while the contraction of ventricular muscle tissue is evidenced by the generation of an R-wave (sometimes referred to as the "QRS" complex when viewed on an ECG strip).

When capture occurs, the evoked response is an intracardiac P-wave or R-wave that indicates contraction of the respective cardiac tissue in response to the applied stimulation pulse. For example, using such an evoked response technique, if a stimulation pulse is applied to the atrium (hereinafter referred to as an "A-pulse"), any response sensed by atrial sensing circuits of the stimulation device immediately following application of the A-pulse is presumed to be an evoked response that evidences capture of the atria.

However, it is for several reasons very difficult to detect a true atrial evoked response. First, a high energy A-pulse may obscure the evoked response signal, making it difficult to detect and identify. Second, the signal sensed by the atrial sensing circuitry immediately following the application of an A-pulse may be not an evoked response, but noise either electrical noise caused, for example, by electromagnetic interference, or myocardial noise caused by random myocardial or other muscle contraction.

Another signal that interferes with the detection of an evoked response, and potentially the most difficult for which to compensate because it is usually present in varying degrees, is lead polarization. A lead/tissue interface is that point where an electrode of the lead contacts the cardiac tissue. Lead polarization is commonly caused by electrochemical reactions that occur at the lead/tissue interface due to application of an electrical stimulation pulse, such as the A-pulse, across the interface. Unfortunately, because the atrial evoked response is sensed through the same lead electrode through which the A-pulse is delivered, the resulting polarization signal formed at the electrode can corrupt the evoked response sensed by the atrial sensing circuits. Furthermore, the lead polarization signal is not easily characterized; it is a complex function of the lead materials, lead geometry, tissue impedance, stimulation energy, and other variables, many of which are continually changing over time.

In each case, the result may be a false positive detection of an atrial evoked response. Such an error leads to a false atrial capture indication, which in turn leads to missed heartbeats—a highly undesirable and potentially a life-threatening situation. Another problem results from a failure by the stimulation device to detect an atrial evoked response that has actually occurred. In this case, a loss of atrial capture is indicated when atrial capture is in fact present—also an undesirable situation that will cause the stimulation device to unnecessarily invoke the atrial pacing threshold determination function and result in higher than necessary stimulus energy values.

Because of the problems previously stated regarding the test for atrial capture verification and automatic threshold tests, currently available stimulation devices do not have this capability. As a result, many medical practitioners manually conduct atrial capture verification tests during periodic follow up examinations. These periodic follow-up examinations are performed by the medical practitioner after initial implantation and configuration of the stimulation device to determine whether the therapy delivered by the device is having the desired effect and to verify the proper operation. Capture verification and pacing threshold assessment is typically performed by the medical practitioner using an external programmer for controlling the stimulation device functions in conjunction with a surface electrocardiogram (ECG) device.

However, this common capture verification and pacing threshold assessment procedure is a time consuming and complex task requiring significant attention and effort on the part of the medical practitioner. The medical practitioner must spend a significant amount of time placing and subsequent removal of ECG electrodes, and configuring the ECG system for the patient's individual characteristics. The practitioner must also manually examine the ECG readout and analyze the cardiac waveform to determine whether capture is present both during initial capture verification and during the pacing threshold determination tests.

It would thus be desirable to provide a system and method for enabling the stimulation device to automatically perform atrial capture verification and atrial pacing threshold determination without a medical practitioner's involvement. It would also be desirable to enable the stimulation device to perform the atrial capture verification and atrial pacing threshold determination without requiring dedicated circuitry and/or special sensors. It would further be desirable to maintain a record of atrial pacing threshold determination in the stimulation device so that a medical practitioner can verify the proper operation of the stimulation device by examining the record.

SUMMARY OF THE INVENTION

The disadvantages and limitations discussed above are overcome by the present invention. In accordance with the invention, a system and method are provided for automating (1) verification of proper atrial capture affected by atrial pacing pulses generated by a patient's implantable cardiac stimulation device, and (2) dynamic adjustment of the device's atrial pacing stimulus energy if and as necessary. The system and method of the present invention do not require use of special dedicated circuitry or special sensors to implement the automated procedures. All of the aforesaid advantages and features are achieved without incurring any substantial relative disadvantage.

The present invention is directed towards the pacing pulse generating portion of an implantable cardiac stimulation device (i.e., a bradycardia pacemaker or the pacing portion of a combination ICD/pacemaker device).

A preferred embodiment of the stimulation device includes a control system for controlling the operation thereof, a set of leads for receiving atrial and ventricular signals and for delivering atrial and ventricular stimulation pulses, a set of sense amplifiers for sensing and amplifying the atrial and ventricular signals, and pulse generators for generating the atrial and ventricular stimulation pulses. In addition, the stimulation device includes memory for storing operational parameters for the control system, and for storing data acquired by the control system for later retrieval by the medical practitioner using an external programmer. The stimulation device also includes a telemetry circuit for communicating with an external programmer.

Preferably, the stimulation device of the present invention is a dual chamber rate-responsive device with atrial tracking modes (such as, DDD and DDD(R)) capable of switching modes to at least a non-tracking mode (such as, DDI and DDI(R)). Accordingly, an activity sensor is also included for sensing when the patient is at, or near, rest.

In a preferred embodiment, the control system periodically performs an atrial capture verification test and an atrial pacing capture threshold assessment test. The frequency with which these tests are to be performed is preferably a programmable parameter set by the medical practitioner using an external programmer when the patient is examined during an office visit or remotely via a telecommunication link. The appropriate testing frequency parameter will vary from patient to patient and depend on a number of physiologic and other factors. For example, if a patient is on a cardiac medication regimen, the patient's atrial capture threshold may fluctuate thus requiring relatively frequent testing and adjustment of the atrial pacing threshold.

In order for the capture verification and threshold assessment tests to work properly, the patient preferably should be at, or near, rest such that a stable atrial rhythm can be monitored by the stimulation device. Thus, prior to initiating atrial capture verification, the control system detects whether the patient is at, or near, rest using the patient activity sensor. If the patient is not at or near rest, the control system waits for a predetermined period of time before attempting to initiate the test again.

When the control system finally determines that the patient is at or near rest, the atrial capture verification test is initiated by first assessing the intrinsic atrial rate or P—P interval. The intrinsic atrial rate must be greater than the base rate such that the intrinsic, or native, P-waves are detectable. When the stimulation device is pacing, the Base Rate must be temporarily programmed to a lower value to allow the intrinsic atrial rate to emerge from the pacing rate. The reprogramming of the Base Rate may be performed in decrements of 5 to 10 ppm until a minimum lower rate, not less than 30 ppm is obtained. The temporary lower rate can be limited by the medical practitioner through the use of the programmer. If the rate of 30 ppm (or the minimum prescribed lower Base Rate of the stimulation device) is reached without the emergence of an intrinsic rhythm, the capture assessment test is automatically terminated.

With the emergence of an intrinsic atrial rate, greater than the Base Rate, the mode of operation is changed from the atrial tracking modes (such as, DDD and DDD(R)) to a non-tracking mode (such as, DDI and DDI(R)). This temporary mode change is necessary to avoid occurrence of a Pacemaker Mediated Tachycardia (PMT) during the testing process. A PMT is a type of arrhythmia that sometimes occurs in VDD or DDD type stimulation devices, in which sensing of retrograde P-waves occurs in the atrium and triggers the ventricle. Retrograde conduction occurs in response to ventricular pacing, causing atrial contraction (i.e. a P-wave). Sensing of this P-wave causes the ventricle to again be stimulated, completing an "endless" loop and thus subjecting the patient to PMT. Switching of the stimulation device into DDI mode eliminates the triggered response in the ventricle, thus preventing the occurrence of PMT.

After the mode switch, the control system monitors and measures the patient's average P-wave interval over a short period of time, and then defines an expected P-wave "window" of predetermined duration in which P-waves are expected to occur. The control system next generates an A-pulse at a predetermined prematurity time interval prior to the next expected P-wave window and thereafter monitors the expected P-wave window to determine whether a P-wave occurs within the window. The lack of a P-wave within that window indicates that an evoked P-wave occurred as a response to the A-pulse immediately following the A-pulse (i.e., outside the expected intrinsic P-wave window). Thus, if a P-wave is not detected during the window, atrial capture is present. If atrial capture is thus verified, the control system switches the stimulation device back to original atrial tracking mode (i.e., DDD or DDD(R)) and ends the atrial capture verification test.

The presence of a P-wave within the window, on the other hand, indicates that there was no P-wave immediately following the A-pulse and thus no atrial capture. In this case, the control system needs to perform the atrial pacing threshold assessment test to set a new atrial pacing threshold to re-establish atrial capture.

The control system sets atrial stimulation (i.e. the A-pulse) level below the previous atrial pacing level (or at a level that is expected to be below the patient's capture threshold), generates the A-pulse and monitors the window for a P-wave. If a P-wave is again detected within the window, then the control system increments the A-pulse level and then generates the A-pulse at the higher level while monitoring the window. This process continues until a P-wave is no longer present during the window interval.

The control system continues to monitor the window for a predetermined number of pacing cycles to ensure that no P-waves occur within the window, and then records the atrial pacing stimulus energy at the current A-pulse output level as the threshold value and, optionally, adds an additional safety margin to the A-pulse threshold value. The control system records the atrial pacing threshold, the atrial stimulation levels, and other test-related data in the memory, and then switches the stimulation device back to original atrial tracking mode before ending the test.

The incremental atrial pacing threshold test of the present invention significantly differs from previously known approaches because atrial stimulus output is initially set lower than the current threshold and progressively increased until capture occurs, while previously known approaches set initial atrial output at a high level and then decrement until capture is lost. The progressive output increase approach is advantageous over prior approaches because less electrical energy is consumed during the testing process and, moreover, because the window observed by the control system is not "swamped" by high output level pulses.

In an alternate embodiment, the method of incrementally increasing the A-pulse level can also be used in an atrial capture system that employs an "evoked response" detection window following a stimulus, wherein only a paced, or evoked, P-wave in the detection window indicates capture, as is well known in the art.

Optionally, if the patient suffers from sinus bradycardia that is accompanied by retrograde conduction, the expected P-wave window is set to at least a predetermined portion of the cardiac cycle, and the control system then searches for retrograde P-waves within the window. Similarly, presence of retrograde P-waves within the window indicates loss of capture, while lack of retrograde P-waves confirms capture. If necessary, the atrial pacing threshold is assessed and set in the same manner as previously described.

The system and method of the present invention thus automatically verify atrial capture and, when necessary, automatically determine a proper atrial pacing threshold of the patient, without requiring dedicated or special circuitry and/or sensors.

BRIEF DESCRIPTION OF THE DRAWINGS

The above and further features, advantages and benefits of the invention will become apparent in the following description taken in conjunction with the following drawings. It is to be understood that the foregoing general description and the following detailed description are exemplary and explanatory but are not intended to be restrictive of the invention. The accompanying drawings, which are incorporated in and constitute a part of this disclosure, illustrate one of the embodiments of the invention and, together with the description, serve to explain the principles of the invention in general terms. Like numerals refer to like parts throughout the disclosure.

DETAILED DESCRIPTION OF THE PREFERRED EMBODIMENTS

The system and method of the present invention utilize a stimulation device's normal sensing, pulse generating and control circuitry to perform an automatic atrial capture verification and, when necessary, an atrial pacing threshold determination test.

Figure 1:
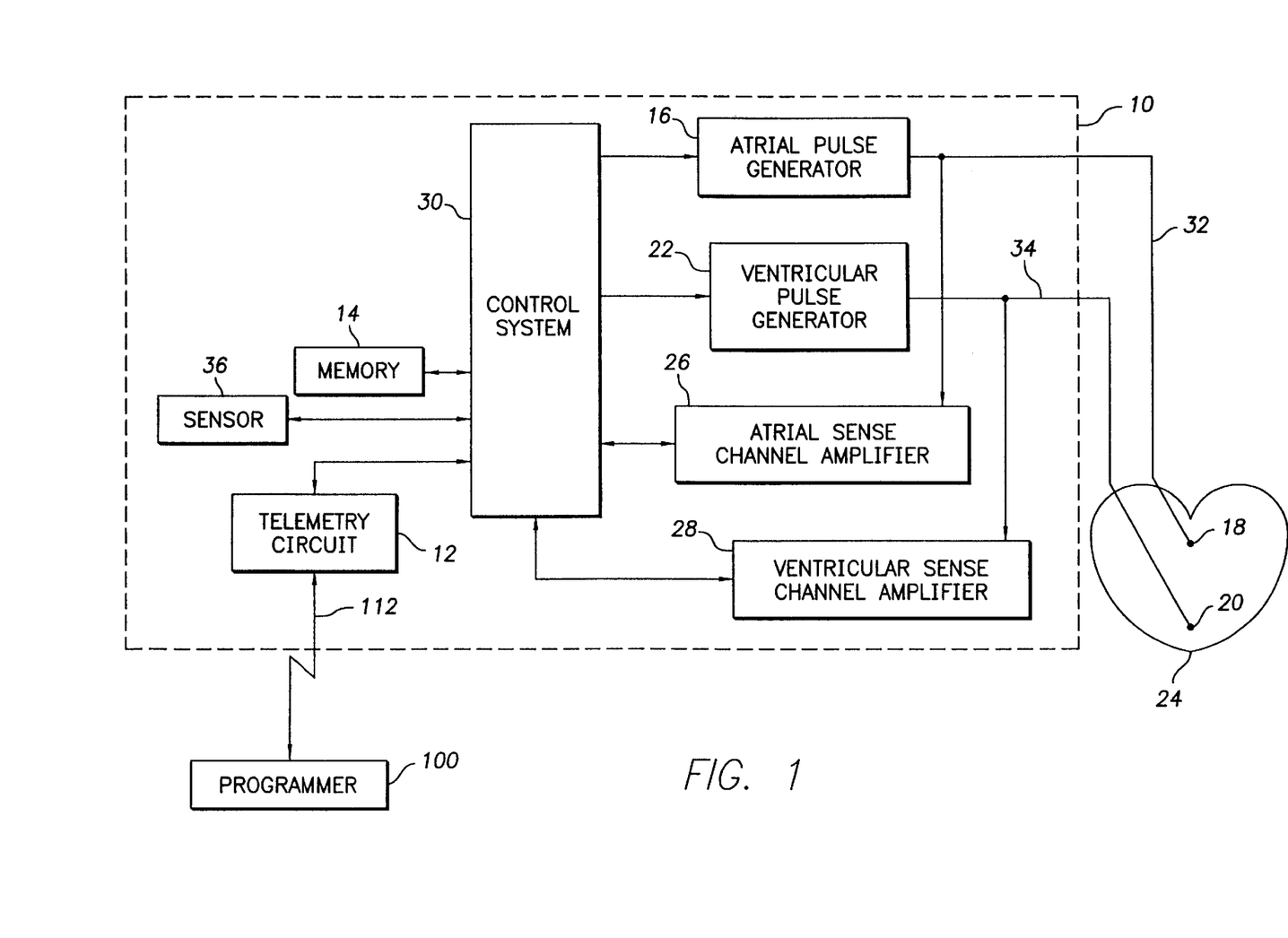
FIG. 1 is a block diagram of a dual chamber stimulation device in accordance with the principles of the present invention.

A stimulation device 10 in accordance with the invention is shown in FIG. 1. The stimulation device 10 is coupled to a heart 24 by way of leads 32 and 34, the lead 32 having an electrode 18 which is in contact with one of the atria of the heart 24, and the lead 34 having an electrode 20 which is in contact with one of the ventricles. The lead 32 carries stimulating pulses to the electrode 18 from an atrial pulse generator 16, while the lead 34 carries stimulating pulses to the electrode 20 from a ventricular pulse generator 22. In addition, electrical signals from the atria are carried from the electrode 18, through the lead 32 to the input terminal of an atrial sense amplifier 26. Electrical signals from the ventricles are carried from the electrode 20, through the lead 34 to the input terminal of a ventricular sense amplifier 28.

Controlling the dual chamber stimulation device 10 is a control system 30. The control system 30 is preferably a microprocessor-based system such as that disclosed in commonly assigned U.S. Pat. No. 4,940,052 of Mann, which is incorporated herein by reference in its entirety. The control system 30 may also be a state logic-based system such as that disclosed in commonly assigned U.S. Pat. No. 4,944,298 of Sholder, which is incorporated herein by reference in its entirety. The control system 30 also includes a real-time clock (not shown) for providing timing functionality for monitoring cardiac events and for timing the application of therapeutic pulses by the pulse generators 16 and 24.

The stimulation device 10 also includes a memory 14 which is coupled to the control system 30. The memory 14 allows certain control parameters used by the control system 30 in controlling the operation of the stimulation device 10 to be programmably stored and modified, as required, in order to customize the operation of the stimulation device 10 to suit the needs of a particular patient. In particular, the pacing stimulus energy parameters for the pacing pulses are stored in the memory 14. In addition, data sensed during the operation of the stimulation device 10, as for example during atrial capture verification and atrial pacing threshold assessment tests, may be stored in the memory 14 for later retrieval and analysis by a medical practitioner using an external programmer.

The control system 30 receives the output signals from the atrial amplifier 26. Similarly, the control system 30 also receives the output signals from the ventricular amplifier 28. These various output signals are generated each time that an atrial event (e.g., a P-wave) or a ventricular event (e.g., an R-wave) is sensed within the heart 24.

The control system 30 also generates an atrial trigger signal which is sent to the atrial pulse generator 16, and a ventricular trigger signal which is sent to the ventricular pulse generator 22. These trigger signals are generated each time that a stimulation pulse is scheduled to be generated by one of the pulse generators 16 or 22. The atrial stimulation pulse is referred to simply as the "A-pulse," and the ventricular stimulation pulse is referred to as the "V-pulse." The characteristics of these stimulation pulses are determined by the pacing stimulus energy settings that are stored in the memory 14.

During the time that either an A-pulse or a V-pulse is being delivered to the heart 24, the corresponding atrial sense amplifier 26 or the ventricular amplifier 28 is typically disabled by way of a blanking signal presented to the appropriate amplifier 26 or 28 from the control system 30. This blanking action prevents the amplifiers 26 and 28 from becoming saturated with the relatively large stimulation pulses that are present at their input terminals during pacing pulse delivery. It also prevents residual electrical signals (known as "after-potentials" or polarization) present at the electrode tissue interface from being interpreted as atrial or ventricular events. During the atrial capture verification and atrial pacing threshold assessment tests of the invention, the atrial sense amplifier 26 is preferably enabled so that P-waves may be detected during all portions of the pacing cycle.

The stimulation device 10 also includes an activity sensor 36 connected to the control system 30 for determining whether the patient is at or near rest. The activity sensor 36 is typically used in rate-responsive stimulation devices to alter the pacing rate to match the patient's physical activity. The control system 30 will only initiate the tests when it determines that the patient is at or near rest.

A telemetry circuit 12 is further included in the stimulation device 10 connected to the control system 30. The telemetry circuit 12 may be selectively coupled to an external programmer 100 by means of an appropriate communication link 112, such as an electromagnetic telemetry link or a remote communication link such as a pair of modems interconnected via a telecommunications link and equipped with telemetry capabilities.

The operation of the stimulation device 10 is generally controlled by a control program stored in the memory 14 and executed by the control system 30. This control program typically consists of multiple integrated program modules, with each module bearing responsibility for controlling one or more functions of the stimulation device 10. For example, one program module may control the delivery of stimulating pulses to the heart 24, while another may control the verification of atrial capture and atrial pacing threshold determination. In effect, each program module is a control program dedicated to a specific function or set of functions of the stimulation device 10. The control program module dedicated to controlling the atrial capture verification and atrial pacing threshold determination tests is described below in connection with FIG. 2.

Figure 2:
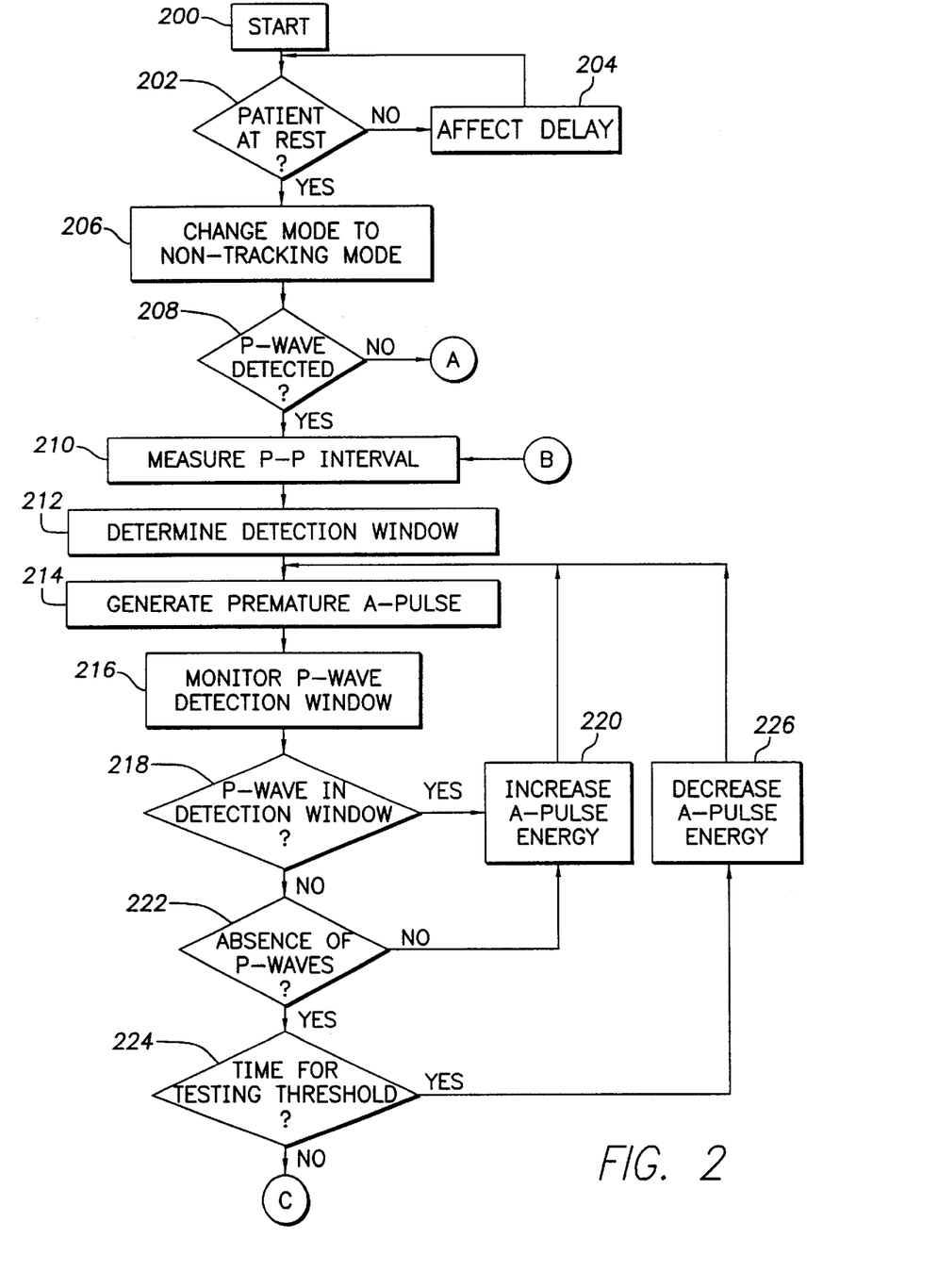
FIGS. 2, 3 and 4 are logic flow diagrams representing an automatic atrial capture verification and atrial pacing threshold determination control program executed by the control system of the stimulation device of FIG. 1, in accordance with one illustrative embodiment.
Figure 3:
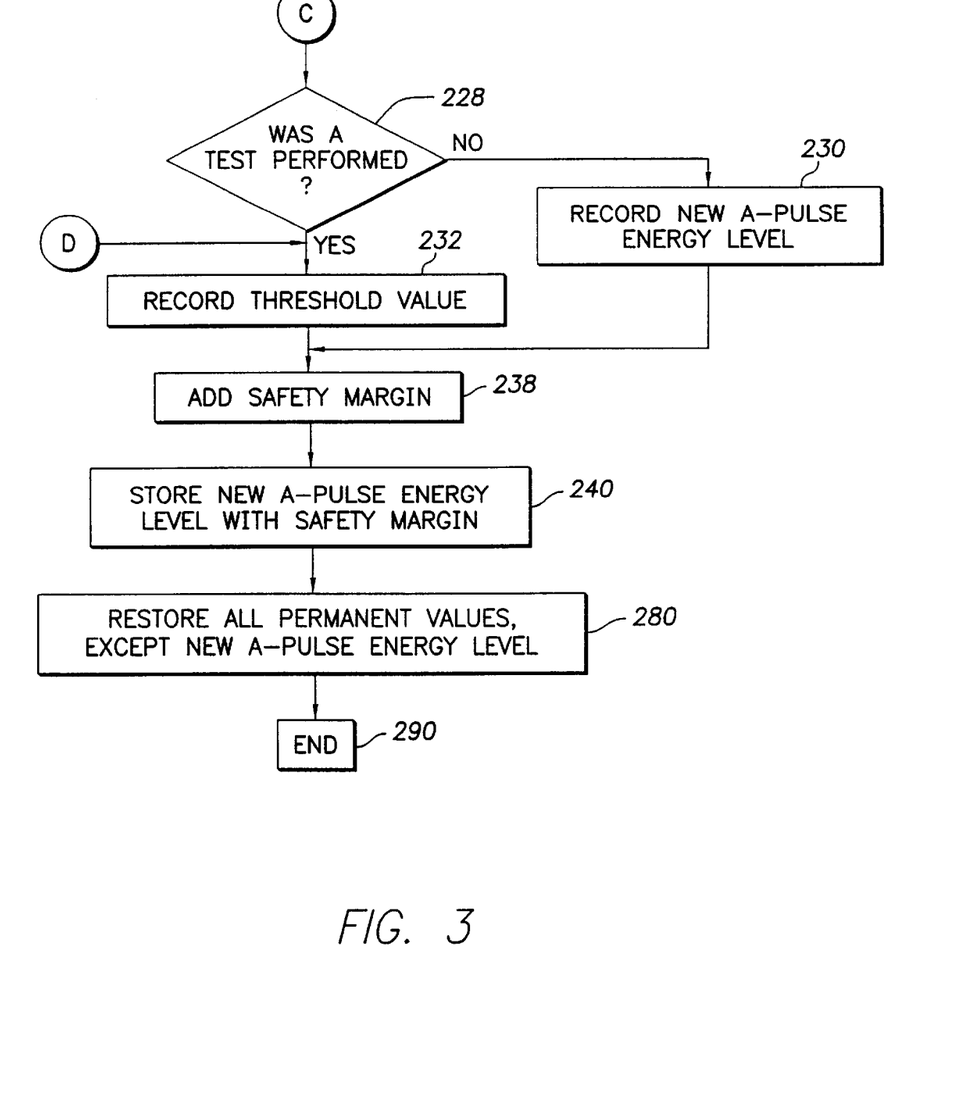
Figure 4:
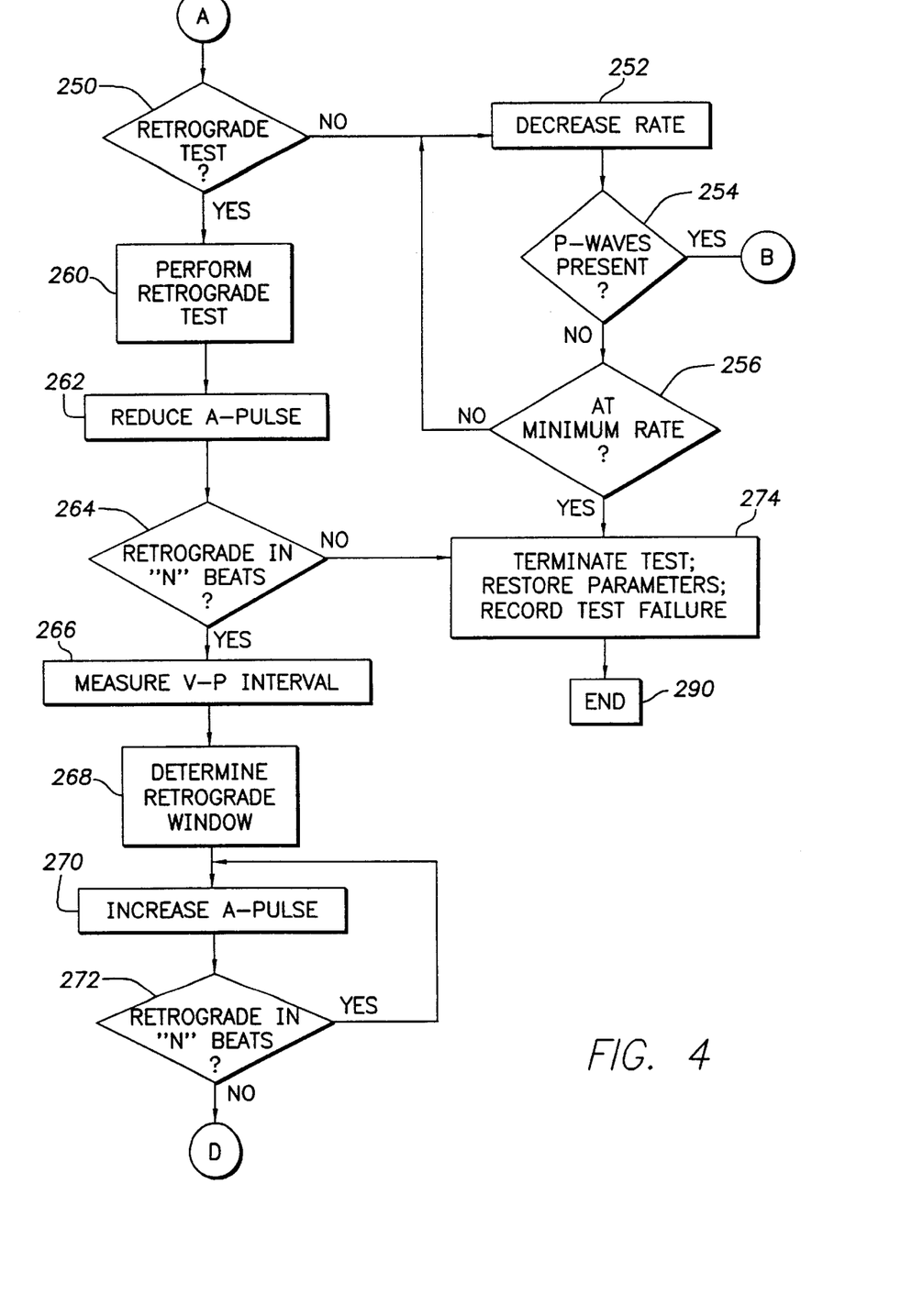

FIGS. 2–4 are a flow diagram representing the control program for assessing atrial capture and performing an atrial capture threshold assessment test.

In a preferred embodiment of the invention, the control system 30 periodically invokes the control program to perform the atrial capture verification test and the atrial pacing threshold assessment tests. The frequency with which these tests are to be performed is preferably a programmable parameter set by using the external programmer 100. Alternatively the programmer may be used to initiate a test sequence when the patient is examined during an office visit or remotely via the communication link 112. The appropriate testing frequency parameter will vary from patient to patient and depend on a number of physiologic and other factors. For example, if a patient is on a cardiac medication regimen, the patient's atrial capture threshold may fluctuate, thus requiring relatively frequent threshold testing and adjustment of the atrial pacing stimulus energy.

There are three different patient conditions during which the capture verification test and the atrial pacing threshold assessment tests may be performed. Most commonly each patient will exhibit one or two of the conditions and rarely only all three conditions. The three conditions usually do not exist simultaneous but, may be present in combination at various times in the same patient. The conditions may dependent upon the patient's daily level of activity, drug regime and time of day. Additionally, the condition may change within each patient as a function of the progression of the disease process expressed as the indications for having a stimulation device implanted and the associated symptoms.

The three patient conditions may be described as (a) an intrinsic atrial rhythm with a rate greater than the programmed Base Rate, (b) an intrinsic atrial rhythm that is over shadowed by pacing at a rate greater than the intrinsic atrial rate, and (c) a paced atrial rhythm where the intrinsic rate is very slow (i.e., in some patients with a very slow intrinsic rhythm, the patient may be symptomatic when paced in a DDD mode at the low atrial rate due to insufficient cardiac output resulting in low peripheral perfusion). Accordingly, each condition will be described separately below.

INTRINSIC ATRIAL RATE>THE PROGRAMMED BASE RATE

As shown in FIGS. 2–3, and with reference to FIG. 1, when the test sequence is initiated (at step 200) and the patient's condition is one where the intrinsic atrial rate is greater than the programmed Base Rate, the control system 30 first determines whether the patient is at, or near, rest (at step 202). Being at rest, provides the best opportunity for detecting when the atrial rhythm and rate are stable. During step 202, the sensor 36 provides comparative information to the control system 30 to detect the rest state. If the patient is not at, or near, rest, the initiation of the test sequence is delayed by an amount of time (at step 204) and then the test for the patient to be at, or near rest, is reassessed.

Once rest is detected (at step 202), the mode is temporarily changed from an atrial tracking mode (i.e., DDD) to a non-atrial tracking mode (i.e., DDI) (at step 206). This mode change prevents the stimulation device from tracking a retrograde P-wave, thus preventing a Pacemaker Mediated Tachycardia (PMT).

The control system 30 next tests for the presence of an intrinsic atrial rate (at step 208) and measures the average P—P interval (at step 210) over sufficient period of time to verify that the patient's atrial rhythm is stable. A stable atrial rhythm and rate will consistently produce P-waves in a defined detection window as determined in step 212. The detection window frequency and duration is calculated by the control system 30 and is dependent upon the measured P—P interval.

The capture verification assessment test proceeds with an A-pulse generated (at step 214) at a predetermined "prematurity" interval, i.e., the generated premature A-pulse will be delivered within a cardiac cycle prior to the occurrence of the P-wave detection window and after the previous detected paced or sensed ventricular beat. The amplitude of the A-pulse is typically predetermined (i.e., programmable or set by the manufacturer). The control system 30 will monitor for P-waves (at step 216) within the predetermined detection window found (at step 212).

Capture by the premature A-pulse is initially detected by the absence of a P-wave in the detection window as determined (at step 218). If capture is detected (that is, no P-waves are occurring in the detection window, (at step 218), then the control system 30 will continue to monitor the absence of P-waves in the detection window for, a predetermined number, "N", of cycles and further may apply additional criteria (e.g., "F" out of "N" cycles) (at step 222).

If either a P-wave is found in the detection window (yes in step 218) or there has not been a predetermined number of cycles without P-waves (no in step 222), then capture is not confirmed and the A-pulse will be incremented in step 220.

Once the capture has been found (at step 222), the control system 30 will check to see if it is time to perform a capture threshold test, (at step 224), to re-establish the lowest threshold.

If it is time for such a test, the A-pulse stimulus amplitude is temporarily decreased to a value expected to be below threshold (at step 226) (e.g., a minimum predetermined value or a value less than the previously recorded threshold value). At this point the loop sequence repeats itself: a premature A-pulse is generated (step 214); the control system 30 monitors for a P-wave within the P-wave detection window (step 216); if a P-wave is detected (step 218), then the A-pulse stimulus amplitude is incremented (step 220); and this loop is repeated until the absence of a P-wave is detected (e.g., in "F" out of "N" P-waves) (step 222).

If it is not time for a threshold test (no, at step 224), the control system 30 continues to "C" in FIG. 3. At step 228, the control system 30 determines whether a capture assessment test was performed, or simply a capture recovery for a single loss of capture. If a capture assessment test was performed, then the A-pulse stimulus amplitude is recorded as the stimulus threshold value (step 232). If it was a capture recovery, then the new value of the pulse energy is recorded and used until it is time for the next capture assessment test. In either case, a safety margin is added (step 238) and store the new A-pulse stimulus value (including the safety margin) into memory 14 (step 240). Finally, the control system 30 will restore all previously programmed parameter values (excluding, of course, the A-pulse stimulus amplitude) in step 280 and end the sequence in 290 (i.e., continue with other pacing routines).

INTRINSIC ATRIAL RATE<THE BASE RATE

As shown in FIGS. 2 and 4, when the patient's condition is one where the intrinsic atrial rate is less than the programmed Base Rate, the control system 30 will determine (at step 208, FIG. 2) that the stimulation device is pacing the atrium because the intrinsic atrial rate is less than the Base Rate of the stimulation device (no, at step 208).

As such, the control system 30 will proceed to step 250 (see "A" in FIG. 4), and determines whether one of the following modes has been pre-programmed based on prior knowledge of what the patient can best tolerate: (a) temporarily decrementing the Base Rate, or (b) perform a retrograde conduction test (at step 250). For the moment, the description below will describe option (a) and discuss option (b) thereafter.

Accordingly, the control system 30 proceeds to step 252 and temporarily decreases the Base Rate based on the prior knowledge that this particular patient can tolerate a temporary lower heart rate that originates from a slow atrial rate.

For the condition that the temporary Base Rate value is greater than the minimum allowable lower rate value, the control system tests for the presence of an intrinsic P-waves (at step 254), and preferably that the P-waves repeat with consistency (e.g., by verifying that there are at least "F" out of "N" P-waves).

When P-waves do not exist with the desired consistency (no, at step 254), indicating that a paced atrial rhythm is detected, the control system 30 proceeds to step 256 to determine if the new temporary Base Rate is equal to the minimum allowable value which is predetermined and stored in memory 14. If it is not, then an additional temporary decrement of the Base Rate occurs (at step 252). This sequence is repeated until such time as the intrinsic atrial rhythm emerges or the minimum allowable Base rate is reached.

If, the minimum temporary Base Rate is reached (at step 256), and an intrinsic atrial rhythm has not emerged, as tested at step 254, the entire test will be terminated, the original pacing mode and other parameters are restored, and the test failure may be date and time stamped and recorded (at step 274) and the test sequence ends (at step 290). The test failure information can be retrieved later via telemetry with the external programmer 100.

When P-waves do exist with the desired consistency (yes, at step 254), the control system 30 proceeds to step 210 ("B" in FIGS. 2 and 4) and the method steps 210–290, of establishing a detection window and for assessing whether P-waves fall within this window, then continues, as described above.

INTRINSIC ATRIAL RATE<BASE RATE WITH SYMPTOMS FROM BRADYCARDIA

As also shown in FIGS. 2 and 4, when the patient's condition is one where the intrinsic atrial rate is less than the programmed Base Rate, the control system 30 will again determine (at step 208, FIG. 2) that the stimulation device is pacing the atrium because the intrinsic atrial rate is less than the Base Rate of the stimulation device (no, at step 208).

However, based on the prior knowledge that this particular patient does not tolerate a temporary lower heart rate that originates from a slow atrial rate, the control system 30 will determine that a Retrograde Conduction test is need (at step 250), as previously programmed into the device by the physician. The control system 30 will then proceed with a Retrograde Conduction test (at step 260, in FIG. 4).

The Retrograde Conduction test is preferred when the patient might experience symptoms such as those that result from low cardiac output resulting from the low intrinsic rate and it is performed at the programmed Base Rate. The Retrograde Conduction test begins with the atrial stimulus energy temporarily set to a desired minimum output (at step 262). This is done to effectively simulate VVI pacing while maintaining the stimulation device in the DDI dual chamber mode previously selected (at step 206).

By virtue of the determination of step 208 (FIG. 2), the stimulation device is currently pacing at a rate greater than the patient's intrinsic rate and therefore the patient should be paced in the ventricle without a synchronizing atrial event, paced or sensed, preceding the ventricular stimulus pulse. The lack of a preceding physiologic encourages retrograde conduction of a signal from the paced or naturally depolarized ventricle to the atrium. A retrograde conducted electrical signal results in an atrial contraction, or depolarization, as evidenced by a P-wave. The presence of the P-wave establishes retrograde conduction and could only exist in response to an isolated ventricular contraction not preceded by an atrial depolarization, and a retrograde conduction pathway. An atrial stimulus of sufficient amplitude so as to cause evoke a P-wave prior to the ventricular paced event will block the retrograde conduction pathway such that a retrograde P-wave will not occur soon after the ventricular depolarization.

As shown in FIG. 4, the retrograde P-wave is detected (at step 264) for several (e.g., "N") beats and preferably "F" out of "N" times to ensure consistency. If step 264 is met, the measured interval between the V-Pulse to P-wave for the retrograde conduction is determined (at step 266). A retrograde detection window for the expected P-wave is established based on the average of a series of measured V-Pulse to P-wave intervals (at step 268).

The presence of retrograde conduction is confirmed by P-waves always appearing in the retrograde detection window. Conversely, when a retrograde P-wave is not present in the retrograde detection window in response to an applied atrial stimulus, the absence indicates that the A-Pulse captured the atrium just prior the V-Pulse, thereby causing the retrograde pathway to be refractory to conduction. Thus, the value of the atrial stimulus energy when the retrograde P-wave disappears is the atrial capture threshold.

Accordingly, the atrial stimulus energy is incremented (at step 270) and when the presence of the retrograde P-wave is detected and, preferably, counted as "F" out of "N" cycles (at step 272), atrial capture is not found. The atrial stimulus energy is then incremented again (at step 270) and the retrograde P-wave detection and counting process continues to loop between steps 270 and 272, until retrograde P-waves are not present (no, at step 272). Thus, the value of the atrial stimulus energy when the retrograde P-wave disappears is the atrial capture threshold.

Alternatively, is the Retrograde Conduction test does not satisfy the desired (e.g., "F" out of "N") criteria in step 264, the test is terminated (at step 274), the original pacing mode and other parameters are restored, and the test failure may be date and time stamped and recorded in memory 14 (at step 274) and the test sequence ends (at step 290). The test failure information can be retrieved later via telemetry with programmer 100.

The invention is not limited by the embodiments described above, which are presented as examples only, but can be modified in various ways within the scope of protection defined by the appended patent claims.

What is claimed is:

1. In an implantable stimulation device, a method for detecting atrial capture and for automatically setting an atrial stimulation level, the method comprising:
   detecting retrograde P-waves;
   defining a detection window for a future retrograde P-wave based on the detected retrograde P-waves;
   generating an atrial stimulation pulse at a predetermined interval prior to the detection window;
   detecting non-capture when a retrograde P-wave is sensed during the detection window;
   detecting capture when a retrograde P-wave is not sensed during the detection window; and
   adjusting atrial stimulation pulse energy when non-capture is detected.

2. The method of claim 1, further comprising:
   generating an activity signal having a magnitude indicative of a physical activity level of the patient;
   detecting when the magnitude of the activity signal is less than a predetermined threshold indicating that the patient is at rest; and defining the detection window only when the activity signal indicates that the patient is at rest.

3. The method of claim 1, wherein the implantable stimulation device is a dual-chamber device, the method further comprising:
   operating in an atrial tracking mode;
   determining that an atrial capture assessment is needed;
   switching from the atrial tracking mode to an atrial non-tracking mode when atrial capture assessment is needed; and
   switching from the atrial non-tracking mode back to the atrial tracking mode when atrial capture is present.

4. The method of claim 1, the method further comprising:
   adjusting a stimulation rate so that intrinsic retrograde P-waves occur;
   defining the detection window which will predict a subsequent intrinsic retrograde P-wave.

5. The method of claim 1, wherein the step of adjusting atrial stimulation pulse energy further comprises:
   initially decreasing the atrial stimulation pulse energy to a predetermined low energy level; and
   subsequently incrementing the atrial stimulation pulse energy by a predetermined amount until atrial capture is detected.

6. In an implantable stimulation device, a system for detecting atrial capture and automatically setting an atrial stimulation pulse energy, the system comprising:
   sensing means for sensing intrinsic P-waves;
   pulse generating means for generating atrial stimulation pulses;
   means for setting a retrograde detection window, wherein the P-waves that are expected to occur during the retrograde detection window comprise retrograde P-waves;
   control means for triggering the pulse generating means to generate atrial stimulation pulses at a predetermined interval prior to the retrograde detection window, for detecting non-capture when a P-wave is sensed during the retrograde detection window, and for detecting capture when a P-wave is not sensed during the retrograde detection window; and
   adjusting means for adjusting atrial stimulation pulse energy until capture is detected as indicated by the detected absence of P-waves in the retrograde detection window.

7. The system of claim 6, further comprising:
   activity sensing means for generating an activity signal having a magnitude indicative of a patient's physical activity level;
   means for detecting when the magnitude of the activity signal is less than a predetermined level indicating that the patient is resting; and
   wherein the control means comprises means for defining the retrograde detection window only when the activity signal indicates that the patient is resting.

8. The system of claim 6, wherein the control means further comprises:
   means for determining that an atrial capture assessment is needed;
   means for adjusting a stimulation rate so that intrinsic P-waves occur when an atrial capture assessment is needed;
   means for determining an intrinsic P—P interval; and
   means for defining the retrograde detection window based on a range about the intrinsic P—P interval.

9. The system of claim 6, wherein the implantable stimulation device is a dual-chamber device operable in an atrial tracking mode and an atrial non-tracking mode, wherein the control means further comprises:
   means for determining that an atrial capture assessment is needed;
   means for switching from the atrial tracking mode to the atrial non-tracking mode when atrial capture assessment is needed; and
   means for switching from the atrial non-tracking mode back to the atrial tracking mode when atrial capture is present.

10. The system of claim 6, wherein the adjusting means further comprises:
    means for determining that an atrial capture assessment is needed;
    means for decreasing the atrial stimulation pulse energy to a predetermined low energy level when atrial capture assessment is needed; and
    means for incrementing the atrial stimulation pulse energy by a predetermined amount until P-waves do not occur during the detection window corresponding to the presence of atrial capture.

11. An implantable stimulation device, comprising:
    a sensing circuit that senses P-waves;
    a timing circuit that sets a detection window corresponding to an expected retrograde P-wave;
    a pulse generator that generates atrial stimulation pulses; and
    a control circuit, coupled to the sensing circuit, the timing circuit and the pulse generator, that triggers the pulse generator to generate an atrial stimulation pulse at a predetermined interval prior to the detection window, that detects non-capture when a retrograde P-wave is sensed during the detection window, and that detects capture when a retrograde P-wave is not sensed during the detection window, the control circuit being operative to adjust the atrial stimulation pulse energy until capture is detected.

12. The system of claim 11, further comprising:
    activity sensor that generates an activity signal having a magnitude indicative of a patient's physical activity level;
    a detector that detects when the magnitude of the activity signal is less than a predetermined level indicating that the patient is resting; and
    wherein the control circuit analyzes the detection window for capture threshold management only when the activity signal indicates that the patient is resting.

13. The system of claim 11, wherein the control circuit is configured to adjust a stimulation rate so that intrinsic P-waves occur when an atrial capture assessment is needed, to determine an intrinsic retrograde P—P interval, and to define the detection window based on a range about the intrinsic retrograde P—P interval.

14. The system of claim 11, wherein:
    the implantable stimulation device is a dual-chamber device operable in an atrial tracking mode and an atrial non-tracking mode; and
    the control means is configured to switch from the atrial tracking mode to the atrial non-tracking mode when atrial capture assessment is needed, and to switch from the atrial non-tracking mode back to the atrial tracking mode when atrial capture is present.

15. The system of claim 11, wherein the control circuit is further configured to determine that an atrial capture assessment is needed, to decrease the atrial stimulation pulse energy to a predetermined low energy level when atrial capture assessment is needed, and to increment the atrial stimulation pulse energy by a predetermined amount until P-waves do not occur during the detection window corresponding to the presence of atrial capture.

* * * * *